United States Patent
Wong et al.

(10) Patent No.: US 7,905,155 B2
(45) Date of Patent: Mar. 15, 2011

(54) MULTI-AXIS TEST APPARATUS

(75) Inventors: Shang Jiun Wong, Singapore (SG); Jian Bing Zhao, Singapore (SG); Swee Tiong Tan, Singapore (SG); Ying Wang, Singapore (SG); Chung Poh Ong, Singapore (SG); Kee Ann Chan, Singapore (SG)

(73) Assignee: Seagate Technology LLC, Scotts Valley, CA (US)

( * ) Notice: Subject to any disclaimer, the term of this patent is extended or adjusted under 35 U.S.C. 154(b) by 489 days.

(21) Appl. No.: 12/061,014

(22) Filed: Apr. 2, 2008

(65) Prior Publication Data

US 2009/0249899 A1    Oct. 8, 2009

(51) Int. Cl.
*G01N 17/00*    (2006.01)
(52) U.S. Cl. ...................................................... 73/865.6
(58) Field of Classification Search ................... 73/865.6
See application file for complete search history.

(56) References Cited

U.S. PATENT DOCUMENTS

| | | | |
|---|---|---|---|
| 4,483,203 A | 11/1984 | Capper | |
| 4,848,160 A | 7/1989 | Marshall et al. | |
| 4,863,499 A * | 9/1989 | Osendorf | 96/134 |
| 4,875,374 A | 10/1989 | Pinson | |
| 5,003,254 A | 3/1991 | Hunt et al. | |
| 5,051,094 A * | 9/1991 | Richter et al. | 434/30 |
| 5,277,066 A | 1/1994 | Marshall | |
| 5,641,917 A | 6/1997 | Hurite et al. | |
| 6,903,886 B2 * | 6/2005 | Matsuda et al. | 360/15 |
| 7,059,202 B2 | 6/2006 | Stanos et al. | |
| 7,601,106 B2 | 10/2009 | Gautier | |
| 2005/0088773 A1* | 4/2005 | Yoshida | 360/75 |
| 2005/0162769 A1* | 7/2005 | Yoshida et al. | 360/39 |

* cited by examiner

*Primary Examiner* — Hezron Williams
*Assistant Examiner* — Alex Devito
(74) *Attorney, Agent, or Firm* — Hensley Kim & Holzer, LLC

(57) ABSTRACT

A testing apparatus for testing a device or components of a device is presented. It is desirable to simulate the effects of rotary and other forces as well as environmental factors on various components of devices to optimize design improvements so as to increase the quality of the various components and the device or to increase the length of service of the various components and the device.

24 Claims, 12 Drawing Sheets

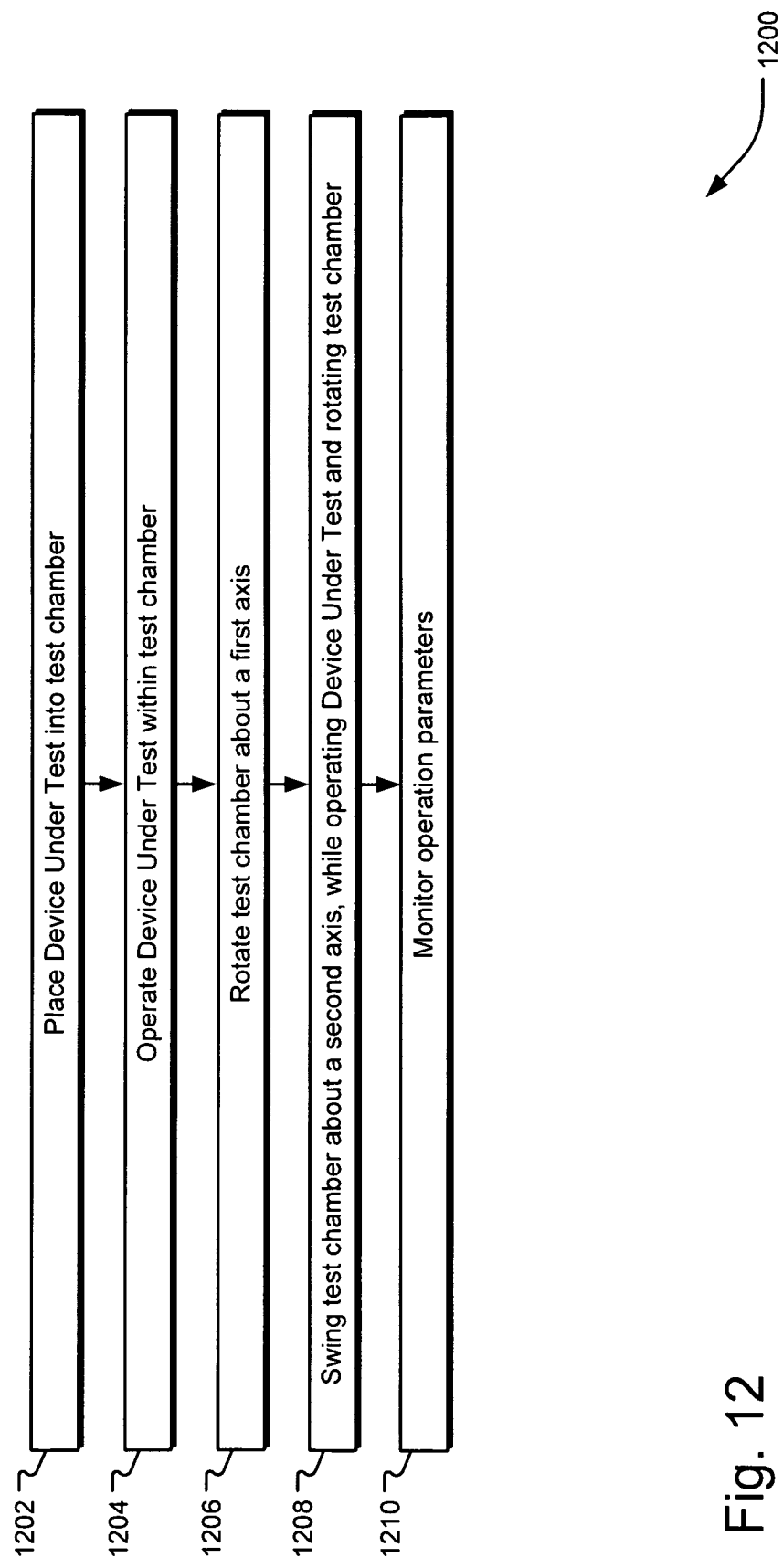

MULTI-AXIS TEST APPARATUS

BACKGROUND

A variety of consumer devices, such as camcorders, cell phones, personal digital assistants, digital music players and the like are exposed to dynamic rotary and linear forces under a variety of environmental conditions. The devices themselves as well as the components thereof—such as memory storage devices, audio/visual components and other components—must endure significant shock and dynamic motion such as when the device is dropped or swung as it is being carried. For example, a user of an device such as a camcorder may swing his or her arm to capture a scene, run or jog with the device to capture another scene, then toss the device into a bag which is then tossed into and around in the back of a vehicle.

Additionally, when used in different environments, the electronic device may be subjected to significant changes in temperature and humidity—for example, tropical climates versus mountainous, desert or arctic climates. Additionally, such devices are often carried in luggage or tote bags that are subjected to vibration, shock or other dynamic forces and environmental factors. Many different types of devices may face similarly challenging conditions, leading to operational problems. It is difficult to simulate the effects of rotary and other dynamic forces as well as environmental factors on various components of devices in a test situation so as to permit design optimization.

SUMMARY

Implementations described and claimed herein provide a testing apparatus for testing a device where the apparatus comprises: a test chamber adapted to hold the device; a first member affixed to and extending from the test chamber, where the first member is adapted to rotate about a first axis; a second member adapted to rotate about a second axis; a joint structure coupling the first member and the second member permitting the first member to rotate the chamber about the first axis while permitting the second member to rotate the first member about the second axis; and control circuitry adapted to operate the device while the first member rotates the chamber about the first axis and the second member swings the chamber about the second axis by rotating the first member about the second axis. In some implementations of this aspect of the testing apparatus, the first member rotation is driven by a first motor. In some implementations of this aspect of the testing apparatus, the second member rotation is driven by a second motor; however, in yet other implementations the second member rotation is driven by a bevel gear, a belt or other driver means.

The test chamber in some implementations includes a device holder or means for securing the device under test to the chamber. The test chamber optionally includes both elements for simulating environmental conditions and elements for monitoring the device during testing. As such, the test chamber may include one or more of: means for counting particulate matter generated by the device during testing, one or more microphones, accelerometers, tri-accelerometers, speakers, vibrators or temperature and/or humidity control means.

Additionally, a method for rotationally testing a device is provided, comprising placing the device in a test chamber; rotating the test chamber about a first axis using a first rotating member; and simultaneously swinging the test chamber about a second axis by rotating the first member about a second axis using a second rotating member.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other features, details, utilities, and advantages of the claimed subject matter will be apparent from the following more particular written Detailed Description of various implementations and implementations as further illustrated in the accompanying drawings and defined in the appended claims.

BRIEF DESCRIPTIONS OF THE DRAWINGS

The described technology is best understood from the following Detailed Description describing various implementations read in connection with the accompanying drawings.

FIG. 12 is a flow diagram of one implementation of a method of use of the testing apparatus.

DETAILED DESCRIPTIONS

A testing apparatus for testing a device or components of a device is presented. Consumer products optimally are built to withstand the ordinary wear and tear to which they are subjected. Moreover, consumers expect greater and greater durability of such products, even with the increasing complexity and utility of the products. In order to optimize design improvements and increase the effective life of devices and the components from which they are constructed, tests are performed on such devices and components, simulating the effects of rotational and other dynamic forces alone or in combination with environmental factors.

The testing apparatus presented provides rotational motion testing comprising two changing axes of rotational motion. Such multi-axis rotational testing is particularly important for components that have rotating parts of significant inertia such as a rotating disc pack assembly in a hard disc drive or other memory storage device. In these components, the rotating parts mimic a gyroscopic device resisting change. In handheld devices such as a camcorder, phone, or music player, it is typical for the device to be subjected to swinging and rocking motions; however, a rotating mass such as a memory storage device component will resist the change in direction due to the gyroscopic effect. Such resistance creates bearing stress, bending, interference and/or friction in the rotating parts, noise, vibration and particle generation in the device, all leading to reduction or failure in reliability of the device.

An example testing apparatus was designed to apply multi-rotational forces on devices or components under test. Such multi-rotational forces simulate real world usage of such devices and components, where arm and wrist actions of the user subject the devices and components to various forces (back and forth swinging, twisting and the like) under a variety of environmental conditions.

For example, in an implementation of the testing apparatus where the device under test is a memory storage device or hard drive, the testing apparatus is capable of assessing the performance of the following drive components under dynamic motion and environmental conditions: the motor fluid dynamic bearing design (including gyroscopic noise and the effects of particle generation and contamination) or other conventional bearings applied in the field, drive read-write head air bearing design (including fly-ability and servo control), pivot bearing design (including gyroscopic noise and the effects of particle generation and contamination), and the effect of particle contamination and heat, cold and/or humidity on the mechanical assembly. For example, the empirical expression to predict head flying and bearing clearance may be generalized to:

$$\text{Clearance} = X_0 - aX_0 - b\Delta P - f(RH)$$

Figure 1:
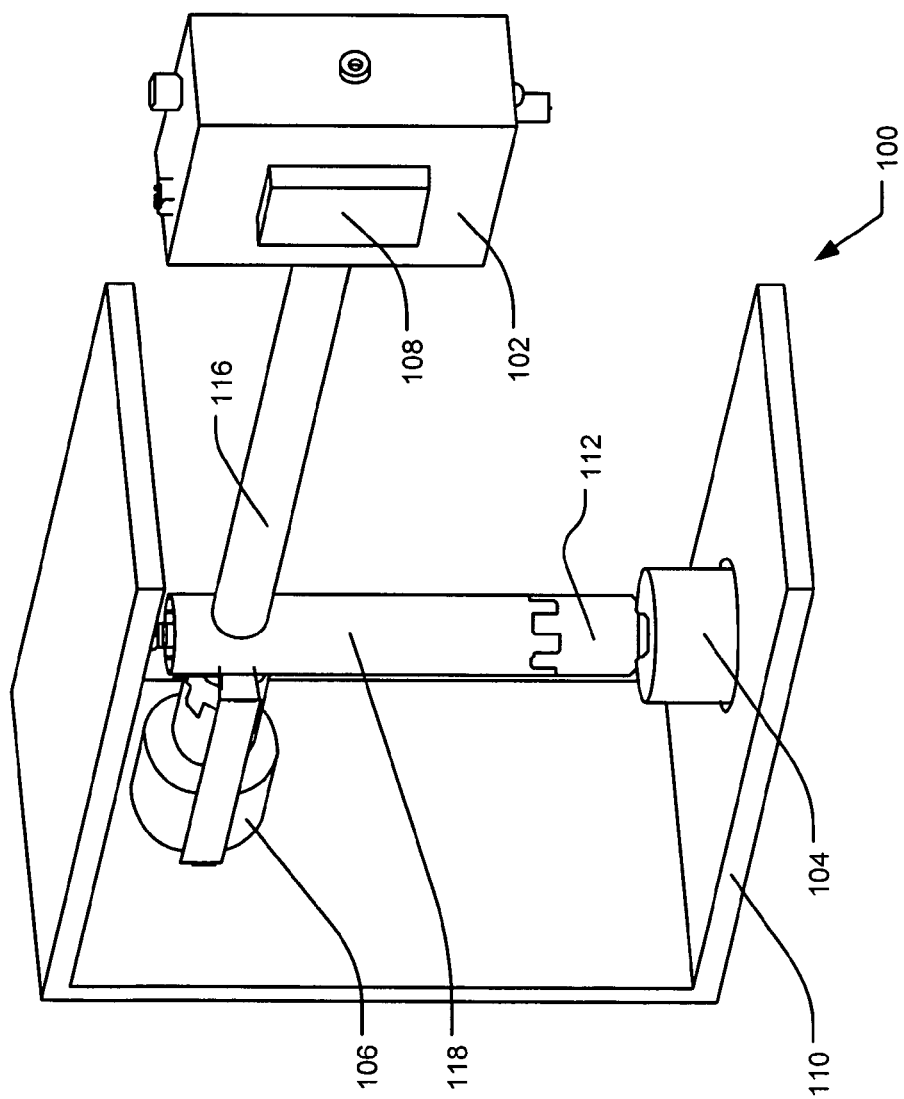
FIG. 1 is an isometric view of one implementation of a testing apparatus.

Where,
$X_0$=Clearance under ambient condition
a=Temperature sensitivity/coefficient
$X_0$=Drive temperature change
b=Altitude sensitivity (for air bearing)
$\Delta P$=Altitude change (kPa)
RH=Relative humidity in the drive Turning now to the Figures, FIG. 1 is an isometric view of one implementation of a claimed testing apparatus. The testing apparatus is shown generally at 100. The testing apparatus 100 includes a test chamber 102 and a stand or housing 110. Other components of the testing apparatus that can be seen in FIG. 1 include a first motor 104, a first coupling 112, a vertical shaft 118, a sleeve 116 that covers the horizontal shaft (not seen) and a second motor 106. In addition, means for holding a device under test can be seen at 108. The stand or housing 110 may be U-shaped as shown in the figures, it may comprise a partial or entire enclosure, or it may comprise one or more ring stands or other supporting structures to support the rotation-inducing mechanisms. In the implementation shown, the test chamber 102 is attached to the sleeve 116 at the side of test chamber 102. In this manner, a rotational element in the device under test can be rotate during test in an axis orthogonal to the axis that the horizontal shaft (not shown) will rotate within sleeve 116. In an alternative implementation, the test chamber may be turned such that the face or back of the test chamber is affixed to the first member. In this manner, a rotational element in the device under test can be rotated during test in the same axis as the axis that the horizontal shaft (not shown) will rotate within sleeve 116.

Figure 2:
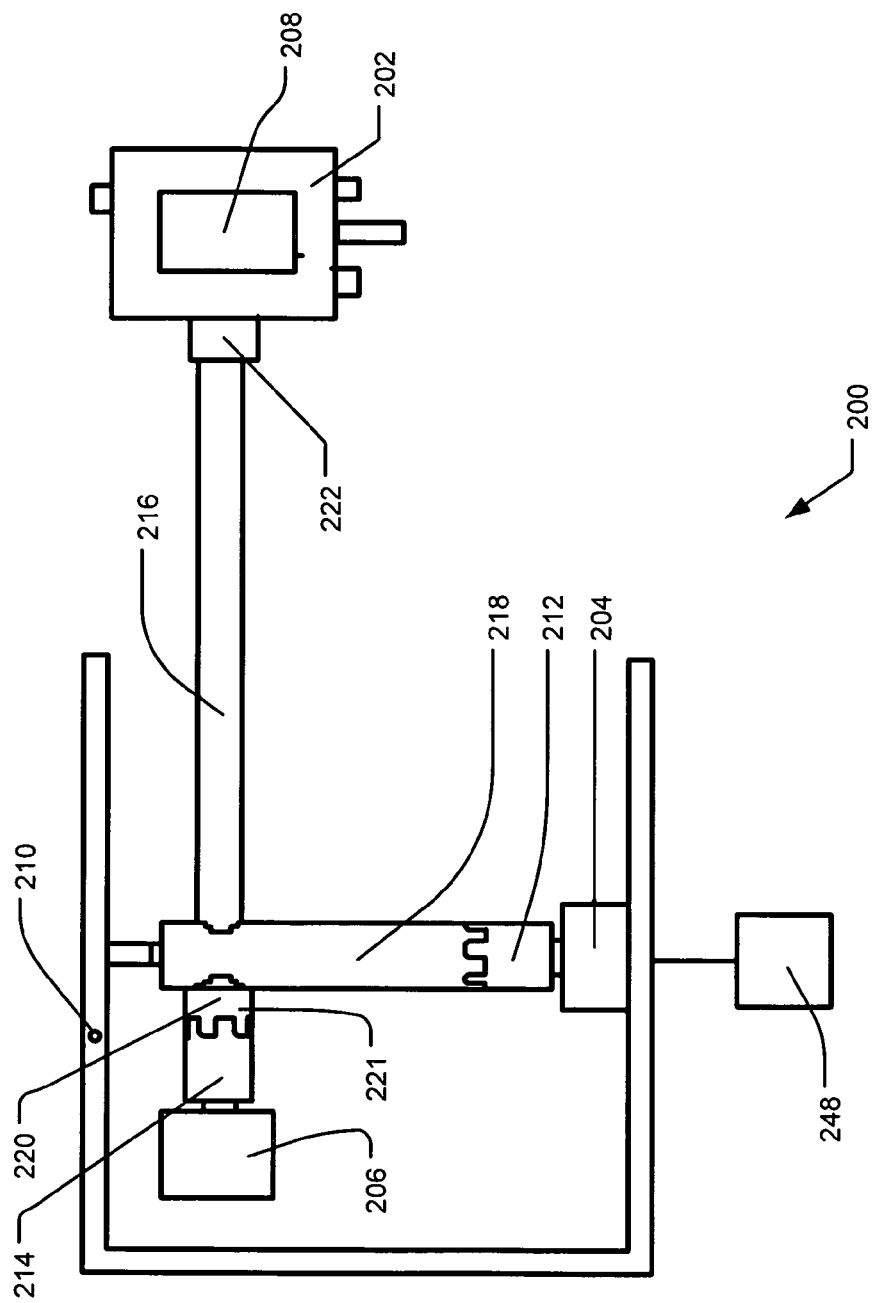
FIG. 2 is a side elevation view of the testing apparatus.

FIG. 2 is a side elevation view of a testing apparatus. Again, the testing apparatus is shown generally at 200, with the test chamber seen generally at 202 and the stand or housing seen at 210. FIG. 2 shows a first motor 204 and a second motor 206. First motor 204 is coupled via coupling 212 to the vertical shaft 218, and rotates vertical shaft 218. Vertical shaft 218 is in turn coupled to horizontal shaft 220 by joint 221 which runs through sleeve 216 and is coupled to chamber 202 via coupling 222. Couplings 217, 214 and 222 in addition to linking the various components of the rotation-inducing mechanisms, may be adapted to smooth the rotational forces as they are applied. A second motor 206 drives the rotation of horizontal shaft 220, which in turn is swung by the rotation of the vertical shaft 218 through joint 221. Means for holding a device under test can be seen at 208. Such a device-holding means may be secured rigidly to the test chamber or the device-holding means may include a suspension system to mimic the device housing in the consumer product in which the device is used. Thus the testing apparatus shown in FIG. 2B has mechanisms to provide two axes of rotation; rotation of vertical shaft 216 driven by motor 204, and rotation of horizontal shaft 218 driven by motor 206. Motors 204 and 206 can be any type of suitable motors known in the art, such as servo motors, and may move the rotating shafts 218 and 220 separately or in a synchronized manner. In some implementations of the testing apparatus, the rotation axes are orthogonal to one another, but the rotational axes can be oriented in any way to simulate the real-world environment of the device under test. In some implementations, the motors can move the vertical and horizontal shafts up to 90°, 120°, 180° or more. FIG. 2 shows control circuitry as a black box at 248. The control circuitry includes control feed-ins to operate the motors 204 and 206, and may also include data feedbacks for monitoring various aspects of the rotational motion being generated, or diagnostics on the motors or other equipment.

Figure 3:
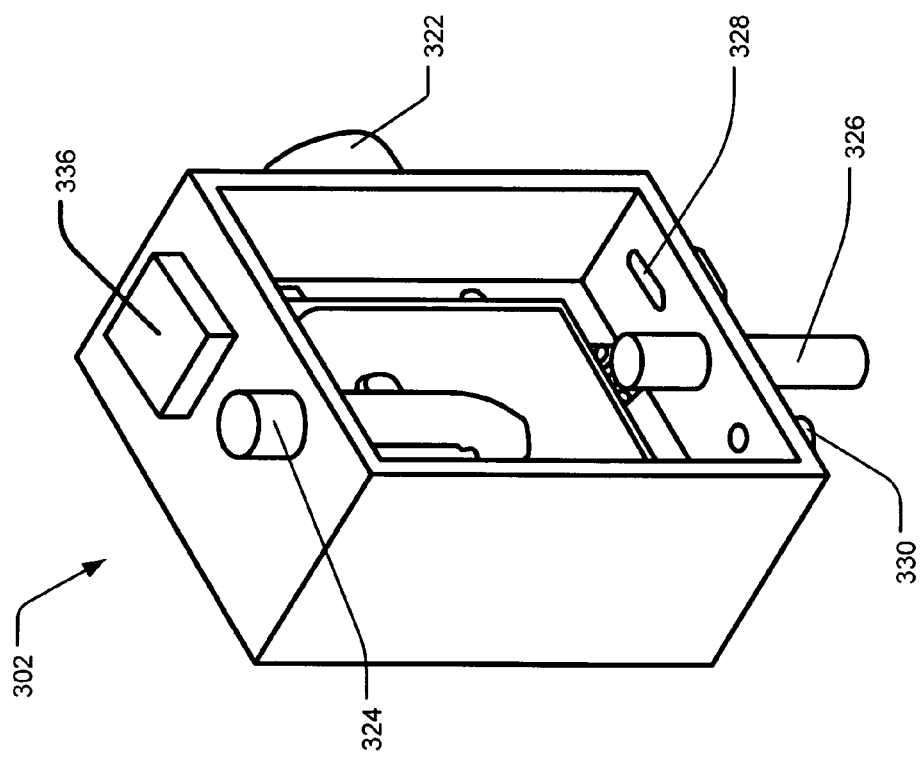
FIG. 3 is a left isometric view of a chamber of a testing apparatus.

FIG. 3 is a left isometric view of a test chamber of a testing apparatus. A test chamber is shown generally at 302. The testing chamber in some implementations will provide a sealing able to withstand the various environmental conditions and dynamic forces used during testing of a device, and in some implementations, the sealing will seal the test chamber 302 if the test chamber is de-pressurized or pressurized (for example, see vacuum port 330). Other exemplary features of the test chamber 302 that are depicted in FIG. 3 include a microphone 326, a port for the passage of cabling, wiring and circuitry in general 328 (including control circuitry, data feedback circuitry and the like), means for counting particles generated by the device under test 324, and a triaccelerometer 336. In addition, coupling 322, which couples the test chamber to the horizontal sleeve 316, is shown.

Figure 4:
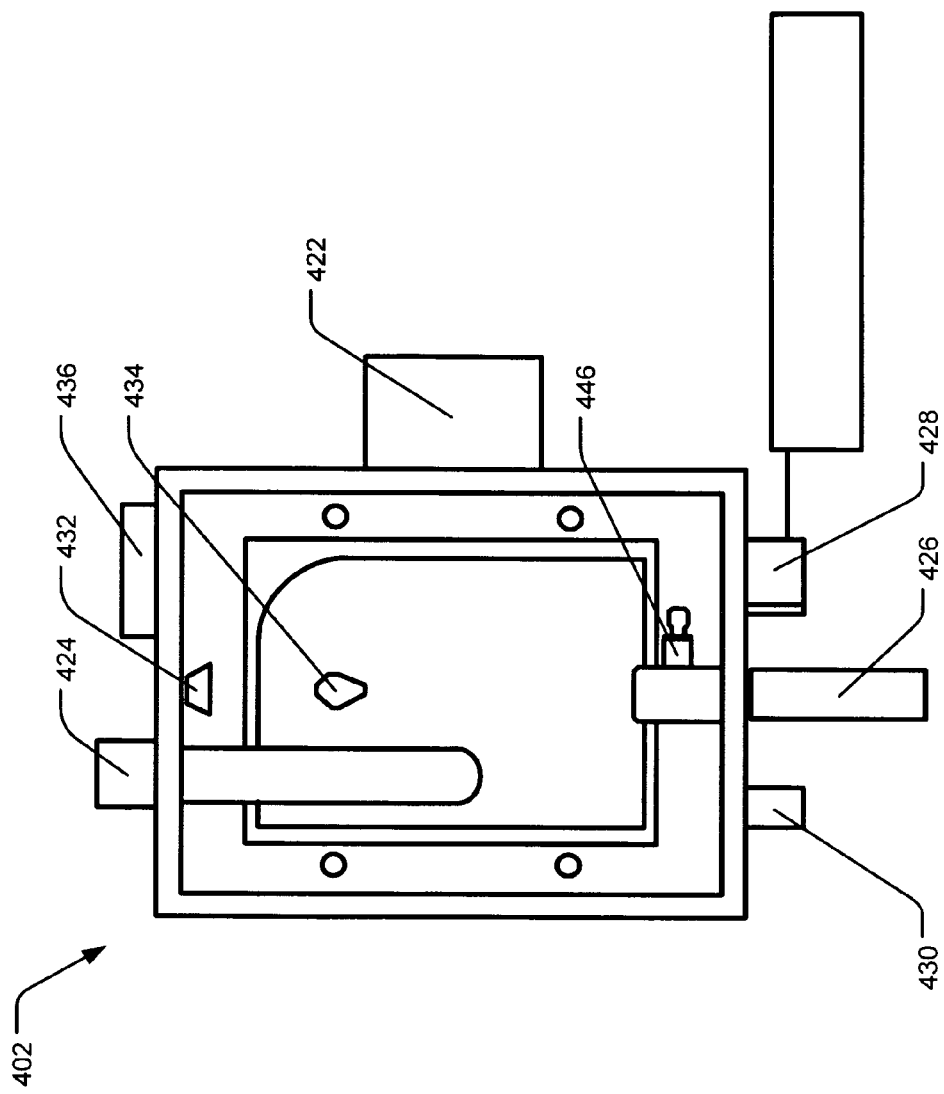
FIG. 4 is a side elevation view of a chamber of a testing apparatus.

FIG. 4 is a side elevation view of a test chamber 402 of a testing apparatus. FIG. 4 depicts a number of elements that simulate environmental conditions, as well as elements that monitor various test parameters. For example, FIG. 4 shows a vacuum port 430 which allows the test chamber to be de-pressurized during testing. Conversely, vacuum port 430 may be used to subject the interior of the chamber (and the device undergoing testing) to pressures greater than ambient pressure. Changes in pressure in the test chamber simulate various environmental conditions that may be encountered by the device undergoing testing in a real world environment. For example, memory storage devices operate in a vacuum and optionally are tested under vacuum. Cable or wiring port 428 is provided so that circuitry for powering and controlling the various simulation elements and monitoring elements can pass into and out of the test chamber. Data feed-in and feedback circuitry may pass into and out of the test chamber via cable or wiring port 428 as well. In addition, simulation elements such as a vibrator 446 and a speaker 432 can be seen. The vibrator and speaker both generate sound waves in the test chamber 402 to simulate conditions that may be encountered in a real-world environment. In this implementation, the vibrator provides waves with frequencies of about 15 Hz to about 200-300 Hz, where the speaker provides sound waves over a greater dynamic range and higher spectrum, such as from 300-500 Hz to 15 to 20 KHz. In the implementation seen here, two devices are shown; however, sound waves may be generated over the same or an even larger range with a single device or with multiple other devices.

Test chamber 402, in addition to comprising elements that simulate environmental conditions, comprises monitoring elements that monitor the changes in the device undergoing testing. For example, FIG. 4 comprises particle counting means 424, a microphone 426, an accelerometer 434, and a tri-accelerometer 436. Microphone 426 picks up gyroscopic noise, i.e., the sound generated by moving the device under test through the two axes. Triaccelerometer 436 and accelerometer 434 used in this implementation of the testing apparatus detect and measure acceleration in one or more axes and other dynamic forces generated by the rotational mechanisms (rotating shafts 418 and 420), as well as measuring vibrations caused by the gyroscopic noise generated by the device under test or the vibration deliberately induced in the system to simulate environmental factors. The means for monitoring particle generation in the test chamber can be any such means known in the art. Additionally, a coupling 422 is shown that serves to couple the test chamber 402 to the horizontal sleeve (not shown).

Figure 5:
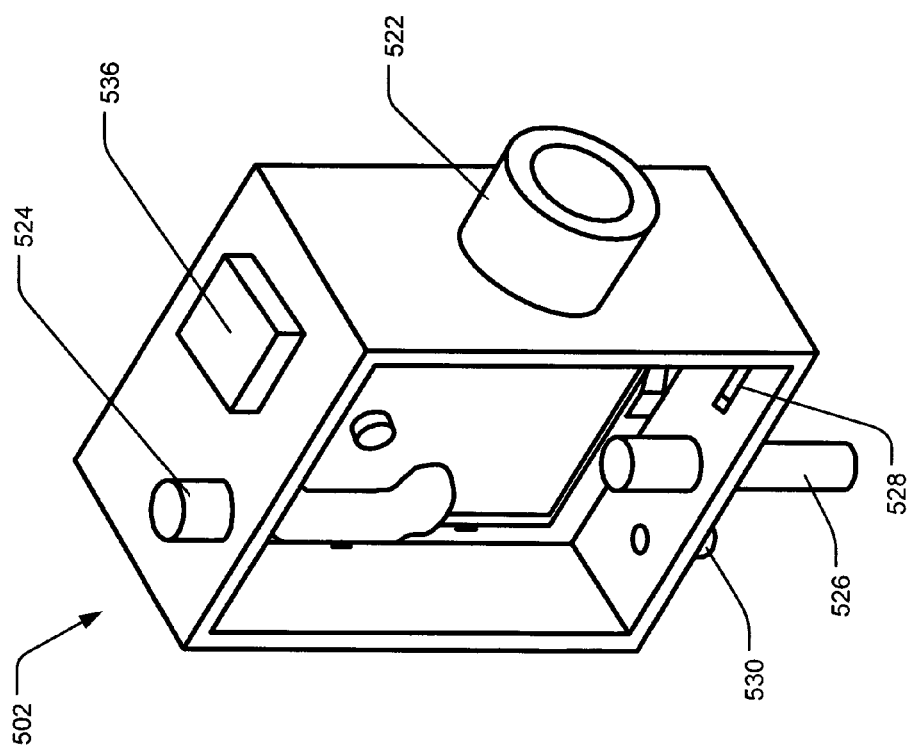
FIG. 5 is a right isometric view of a chamber of a testing apparatus.

FIG. 5 is a right isometric view of a test chamber of a testing apparatus. The test chamber is shown generally at 502. Exemplary features of the test chamber 502 that are depicted in FIG. 5 include a vacuum port 530, microphone 526, a port for the passage of cabling, wiring and circuitry in general 528, means for counting particles generated by the device under test 524, and a triaccelerometer 536. In addition, coupling 522, which couples the test chamber to the horizontal sleeve 516, is shown.

Figure 6:
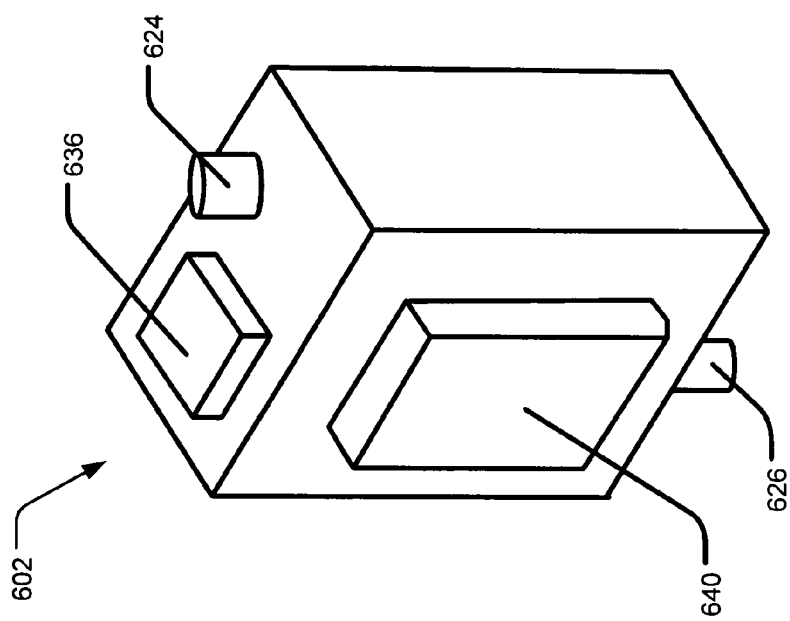
FIG. 6 is a rear isometric view of a chamber of a testing apparatus.

FIG. 6 is a rear isometric view of a test chamber of a testing apparatus. Again, the test chamber is shown generally at 602. Other exemplary features of the test chamber 602 that are depicted in FIG. 6 include a microphone 626, means for counting particles generated by the device under test 624, and a triaccelerometer 636. In addition, a thermal control module 640 is shown. The thermal control module may comprise means for heating and/or cooling the test chamber (or the device under test only), as well as means for monitoring the temperature of the test chamber and/or the device under test. That is, a thermal control module may serve both a simulation function and a monitoring function. Alternatively, separate devices may be used to provide the heating/cooling function and the temperature monitoring function.

Figure 7:
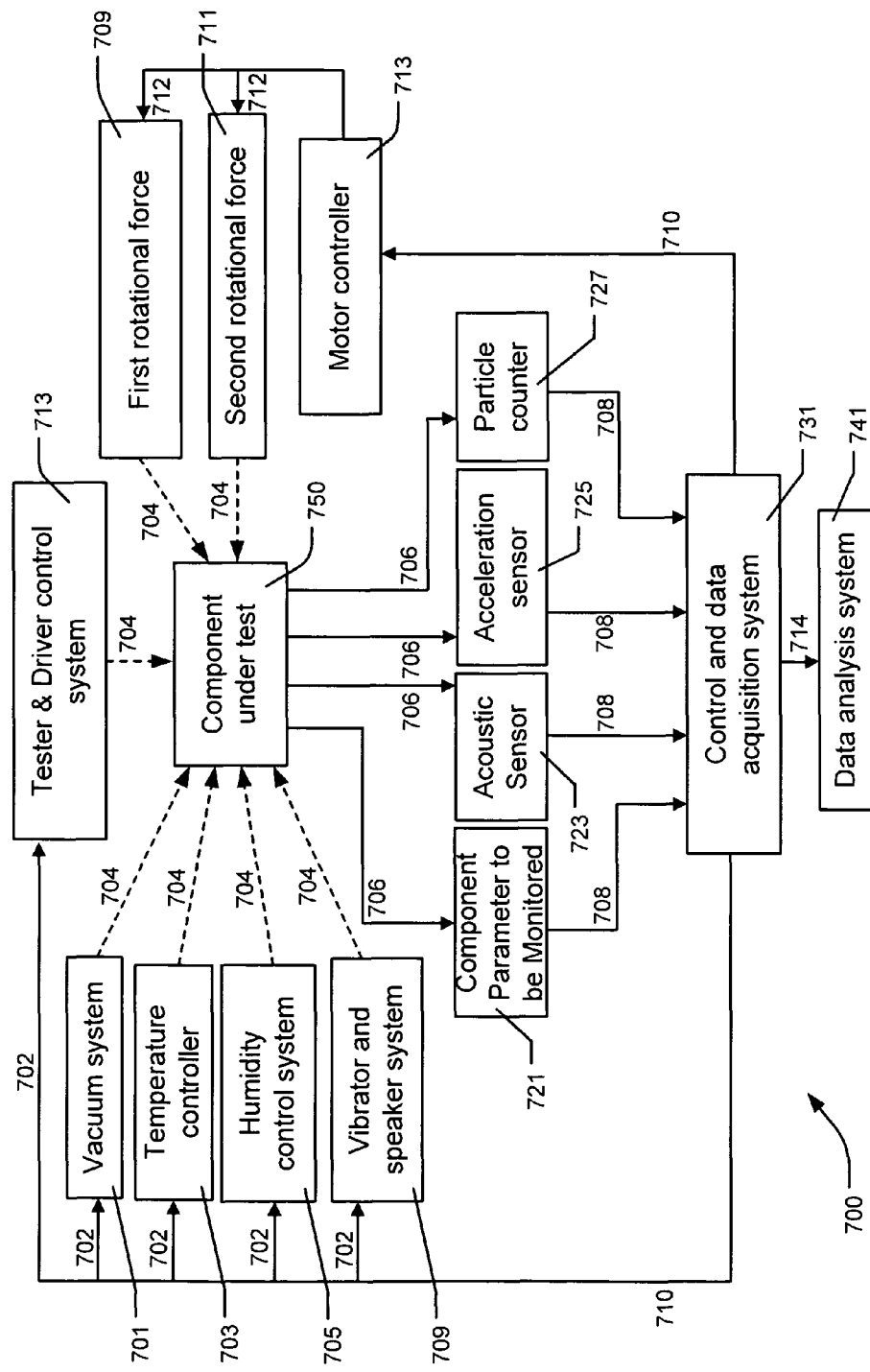
FIG. 7 is a block diagram of various inputs and outputs according to one implementation of the testing apparatus.

FIG. 7 is a block diagram illustrating one implementation of the various inputs and outputs of the testing apparatus. The component under test 750 is subjected (via control inputs 704) to a vacuum system 701, a temperature controller 703, a humidity control system 705, and a vibrator and/or speaker system 707, all controlled by the control and data acquisition system 731 via controls 710 and 702. In addition, the component under test 750 is subjected to a first rotational force 709 and a second rotational force 711, both controlled by the control and data acquisition system 731 via control 710 through the motor controller(s) 713 via controls 712. The component under test 750 is also subjected to the test and drive control system 713 that activates or operates the component under testing during testing via control 704. It should be understood that the implementation shown in this FIG. 7, is exemplary only. Some of the features shown may not be included in some implementations of the device; or other features may be added to test other environmental conditions with yet other parameters being measured.

Again looking at FIG. 7, various aspects of the state of the component under test are monitored, for example via reporting circuitry 706, by an acoustic sensor 723, an acceleration sensor 725, a particle counter 727, or some other monitoring device that gathers data on a component parameter of interest 721. The information processed by monitoring devices 721, 723, 725 and 727 is passed, via circuitry 708 to the control and data acquisition system 731. Information regarding the component under test is passed to a data analysis system 741 via data feed 714. Also, instructions may be sent via control elements 710 to vary different conditions of the various simulators in a feedback loop.

Figure 8:
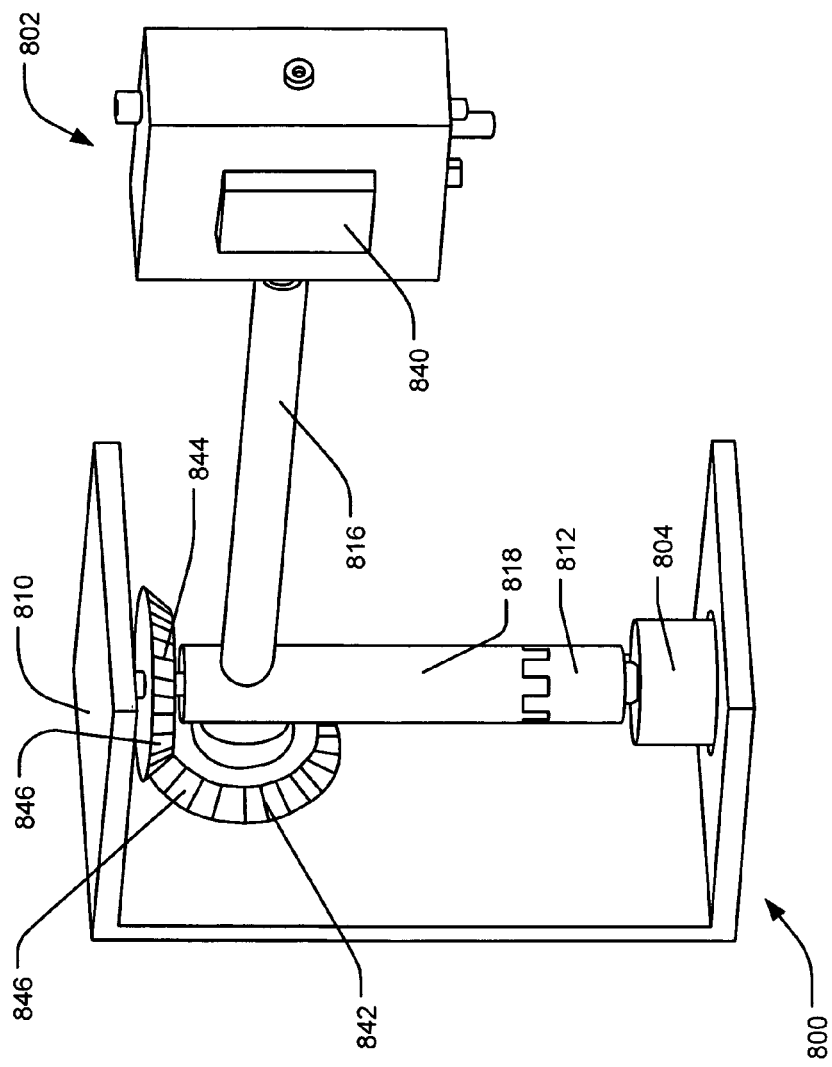
FIG. 8 is an isometric view of one implementation of a testing apparatus according.

FIG. 8 is an isometric view of an alternative implementation of a testing apparatus that is different from that shown in FIGS. 2 and 3. The testing apparatus is shown generally at 800. The testing apparatus 800 includes a test chamber 802 and a stand or housing 810. Means for holding a device under test can be seen at 816. Other components of the testing apparatus that can be seen in FIG. 8 include a first motor 804, a first coupling 812, a vertical shaft 818 and, instead of a second motor, a gear link 846 is shown. Gear link 846 in this implementation comprises a free bevel gear 842 and a fixed bevel gear 844. A thermal control module is shown at 840.

Figure 9:
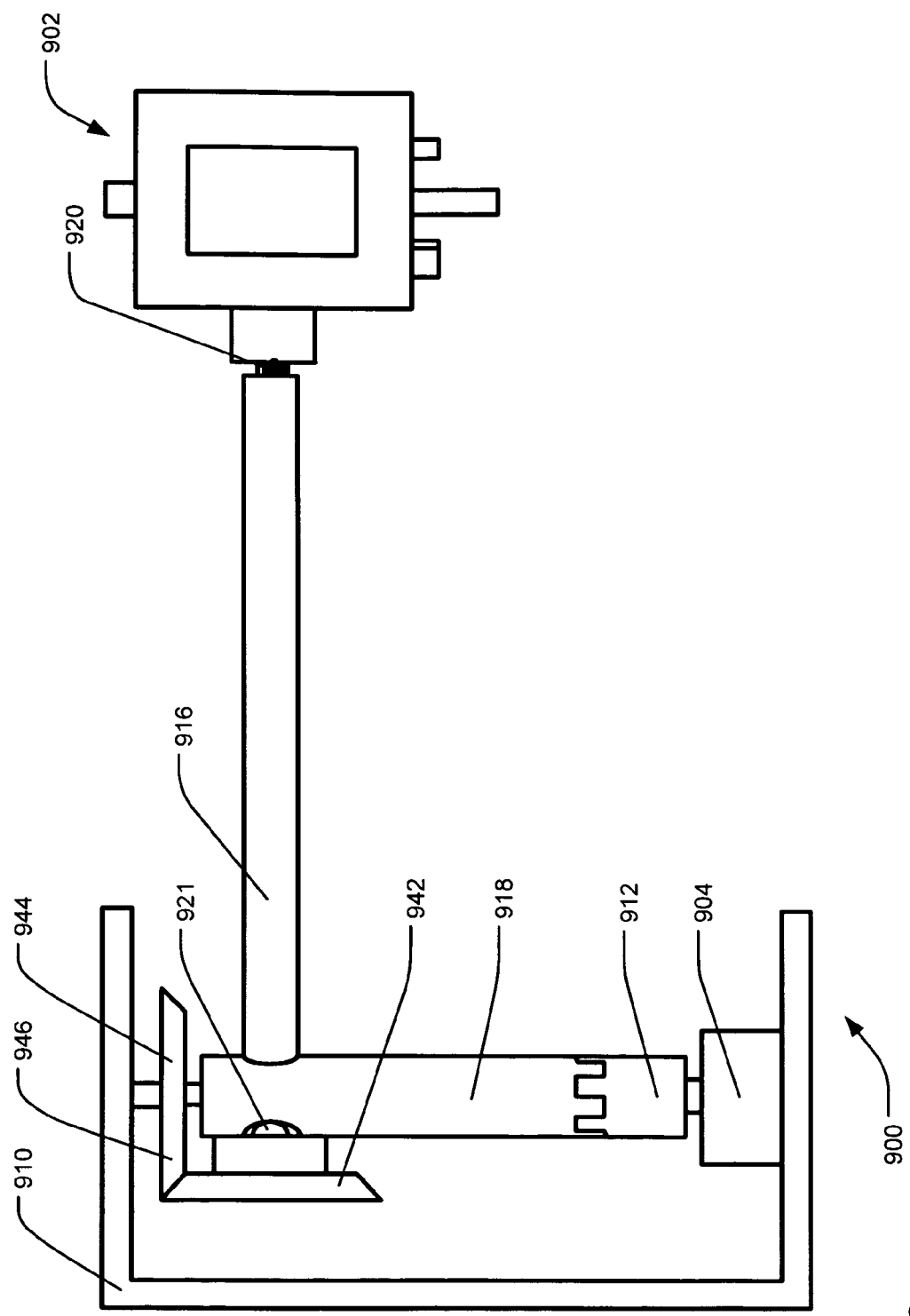
FIG. 9 is a side elevation view of the testing apparatus.

FIG. 9 is a side elevation view of the implementation of the testing apparatus seen in FIG. 8. Again, the testing apparatus is shown generally at 900, with the test chamber seen generally at 902 and the stand or housing seen at 910. FIG. 9 shows the first motor 904 and a gear link 946 comprising a free bevel gear 942 and a fixed bevel gear 944. First motor 904 is coupled via coupling 912 to the vertical shaft 918, and rotates vertical shaft 918. Vertical shaft 918 is in turn coupled to horizontal shaft 920 by joint 921 which runs through sleeve 916 and is coupled to chamber 902 via coupling 922. A second motor 906 drives the rotation of horizontal shaft 920. Means for holding a device under test can be seen at 908. As with the testing apparatus shown in FIGS. 1 and 2, the testing apparatus shown in FIG. 2 has mechanisms to provide two axes of rotation. In yet another implementation, the gear link or second motor can be replaced by a best to drive the second rotating means, or by other driving means known in the art.

Figure 10:
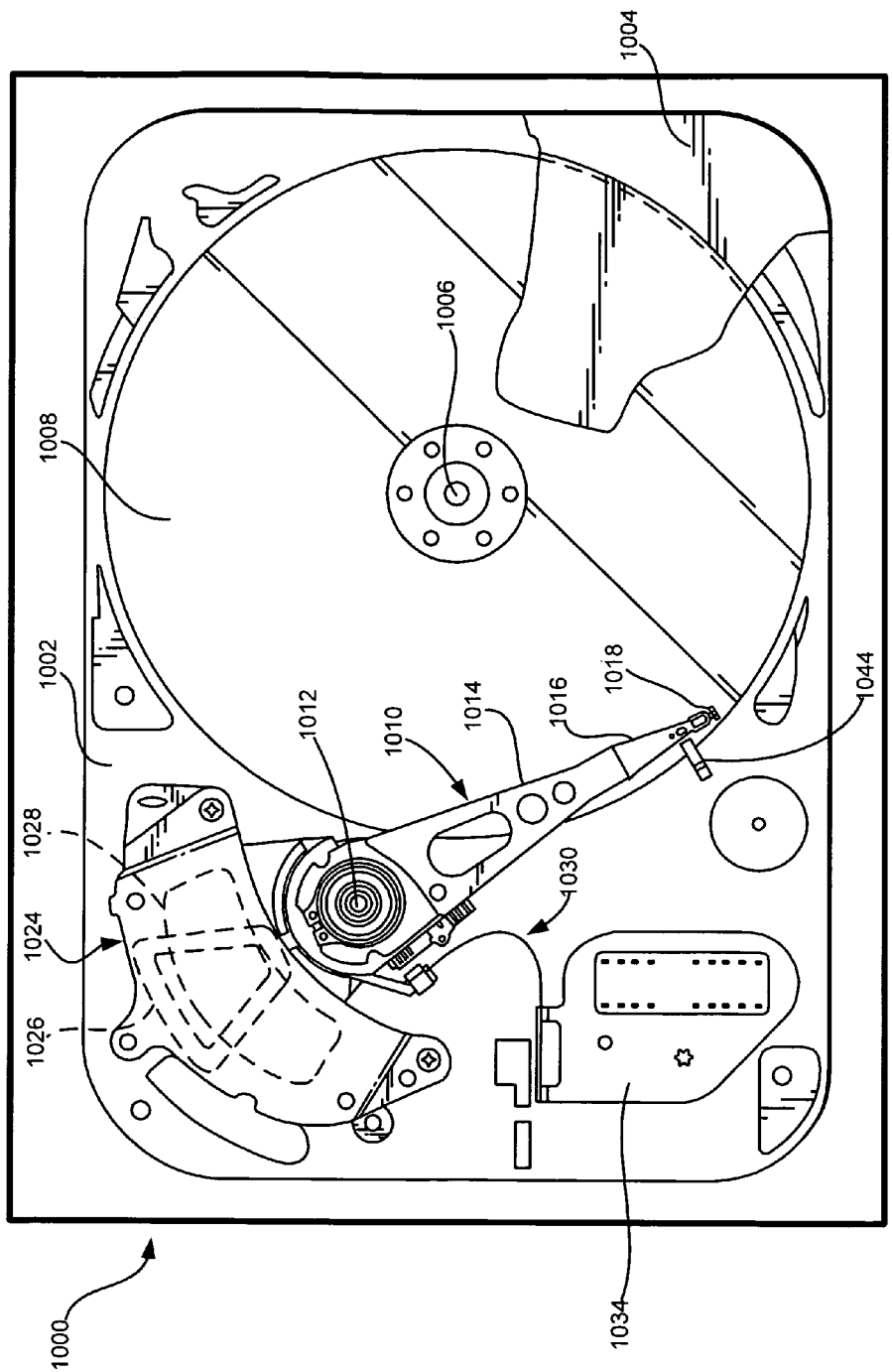
FIG. 10 illustrates a plan view of an example disc drive.

One device that may be tested in the testing apparatus exemplified herein is a hard disc drive 1000, where the multiple axis testing apparatus places the hard disc drive through a range of motions and environmental conditions, allowing designers to optimize the components of the hard disc drive. FIG. 10 illustrates a plan view of an example disc drive 1000 inside test chamber 1050. The disc drive 1000 includes a base 1002 to which various components of the disc drive 1000 are mounted. A top cover 1004, shown partially cut away, cooperates with the base 1002 to form an internal, sealed environment for the disc drive in a conventional manner. The components include a spindle motor 1006 that rotates one or more storage medium discs 1008 at a constant high speed. Information is written to and read from tracks on the discs 1008 through the use of an actuator assembly 1010, which rotates during a seek operation about a bearing shaft assembly 1012 positioned adjacent the discs 1008. The actuator assembly 1010 includes a plurality of actuator arms 1014 that extend towards the discs 1008, with one or more flexures 1016 extending from each of the actuator arms 1014. Mounted at the distal end of each of the flexures 1016 is a head 1018 that includes an air bearing slider enabling the head 1018 to fly in close proximity above the corresponding surface of the associated disc 1080. The distance between the head 1180 and the storage media surface during flight is referred to as the "fly height".

During a seek operation, the track position of the head 1018 is controlled through the use of a voice coil motor (VCM) 1024, which typically includes a coil 1026 attached to the actuator assembly 1010, as well as one or more permanent magnets 1028 which establish a magnetic field in which the coil 1026 is immersed. The controlled application of current to the coil 1026 causes magnetic interaction between the permanent magnets 1028 and the coil 1026 so that the coil 1026 moves in accordance with the well-known Lorentz relationship. As the coil 1026 moves, the actuator assembly 1010 pivots about the bearing shaft assembly 1012, and the heads 1018 are caused to move across the surfaces of the discs 1008.

The spindle motor 1006 is typically de-energized when the disc drive 1000 is not in use for extended periods of time. The heads 1018 are moved away from portions of the disc 1008 containing data when the drive motor is de-energized. The heads 1018 are secured over portions of the disc not containing data through the use of an actuator latch arrangement and/or ramp assembly 1044, which prevents inadvertent rotation of the actuator assembly 1010 when the drive discs 1008 are not spinning. Such a disc drive 1000 may be tested when in an energized state or when in a de-energized state.

A flex assembly 1030 provides the requisite electrical connection paths for the actuator assembly 1010 while allowing pivotal movement of the actuator assembly 1010 during operation. The flex assembly 1030 includes a printed circuit board 1034 to which a flex cable connected with the actuator assembly 1000 and leading to the head 1018 is connected. The flex cable may be routed along the actuator arms 1014 and the flexures 1016 to the heads 1018. The printed circuit board 1034 typically includes circuitry for controlling the write currents applied to the heads 1018 during a write operation and a preamplifier for amplifying read signals generated by the heads 1010 during a read operation. The flex assembly 1030 terminates at a flex bracket for communication through the base deck 1002 to a disc drive printed circuit board (not shown) mounted to the bottom side of the disc drive 1000.

The spindle control circuitry in disc drive 1000 will be controlled, for example, by the circuitry that controls the test chamber, so that the disc drive can be tested while in operation. In an exemplary implementation, the spindle control circuitry in the disc drive 1000 includes a profile datastore that stores driving voltage profile data defining a limited portion of a full driving voltage profile for rotating the spindle motor. The limited portion of the driving voltage profile is limited to one-sixth of the electrical period for completely rotating the spindle motor. In an alternative implementation, the commutation logic circuit is coupled to winding terminals of a spindle motor and drives each winding terminal of the spindle motor with a driving voltage defined by a driving voltage profile that includes for each winding terminal at least one excitation state of the winding terminal saturated at a power supply voltage and at least one excitation state of the winding terminal saturated at a neutral level.

Figure 11:
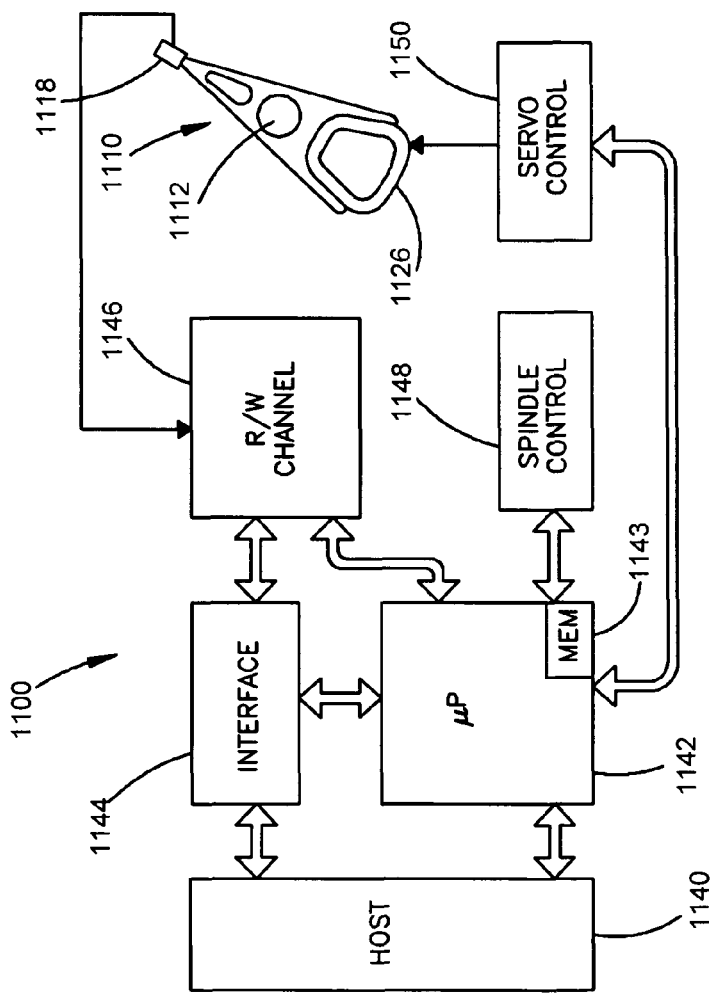
FIG. 11 illustrates the example functional components of a disc drive.

FIG. 11 illustrates the primary functional components of a disc drive incorporating one of the various implementations of the described technology and generally shows the main functional circuits that are resident on the disc drive printed circuit board and used to control the operation of the disc drive. Such a disc drive represent an example device under test that can fit within the test chamber and be tested by the testing apparatus. The disc drive is operably connected to a host computer 1140 in a conventional manner. Control communication paths are provided between the host computer 1140 and a disc drive microprocessor 1142, the microprocessor 1142 generally providing top level communication and control for the disc drive in conjunction with programming for the microprocessor 1142 stored in microprocessor memory (MEM) 1143. The MEM 1143 can include random access memory (RAM), read only memory (ROM) and other sources of resident memory for the microprocessor 1142.

The discs are rotated at a constant high speed by a spindle motor control circuit 1148, which typically electrically commutates the spindle motor through the use, typically, of back electromotive force (BEMF) sensing. During a seek operation, wherein an actuator 1110 moves heads 1118 between tracks on the storage media, the position of the heads 1118 is controlled through the application of current to the coil 1126 of a voice coil motor. A servo control circuit 1150 provides such control. During a seek operation the microprocessor 1142 receives information regarding the velocity of the head 1118, and uses that information in conjunction with a velocity profile stored in memory 1143 to communicate with the servo control circuit 1150, which will apply a controlled amount of current to the voice coil motor coil 1126, thereby causing the actuator assembly 1110 to be pivoted.

Data is transferred between the host computer 1140 or other device and the disc drive by way of an interface 1144, which typically includes a buffer to facilitate high speed data transfer between the host computer 1140 or other device and the disc drive. Data to be written to the disc drive is thus passed from the host computer 1140 to the interface 1144 and then to a read/write channel 1146, which encodes and serializes the data and provides the requisite write current signals to the heads 1118. To retrieve data that has been previously stored in the data storage device, read signals are generated by the heads 1118 and provided to the read/write channel 1146, which performs decoding and error detection and correction operations and outputs the retrieved data to the interface 1144 for subsequent transfer to the host computer 1140 or other device.

In an exemplary implementation, the spindle control circuit 1148 in the disc drive 1100 will in some implementations be controlled by the circuitry that controls the test chamber and may include a profile datastore that stores driving voltage profile data defining a limited portion of a full driving voltage profile for rotating the spindle motor. The limited portion of the driving voltage profile is limited to one-sixth of the electrical period for completely rotating the spindle motor. In one implementation, the spindle motor control circuit 1148 in the disc drive 1100 also includes a commutation logic circuitry coupled to the profile datastore and to winding terminals of the spindle motor. The commutation logic circuitry drives each winding terminal of the spindle motor to completely rotate the spindle motor, wherein at least four of six excitation states of the winding terminal provide driving voltages are defined or derived from the limited portion of the driving voltage profile stored in the profile datastore. In an alternative implementation, the commutation logic circuit is coupled to winding terminals of a spindle motor and drives each winding terminal of the spindle motor with a driving voltage defined by a driving voltage profile that includes for each winding terminal at least one excitation state of the winding terminal saturated at a power supply voltage and at least one excitation state of the winding terminal saturated at a neutral level.

FIG. 12 is a flow diagram of one implementation of a method 1200 for rotationally testing a device. First, the device under test is placed in a test chamber 1202. Next, the device under test is made to be operational within the test chamber 1204. Next, the test chamber is rotated about a first axis 1206, while the test chamber is simultaneously swung about a second axis 1208. Finally, the operational parameters of the device under test are measured 1210. In some implementations, a first member rotates about the first axis, and a second member rotates the first member around a second axis, which rotates the test chamber around a second axis as well.

The above specification, examples and data provide a complete description of the structures of exemplary implementations of apparatus that may be used for testing apparatus and components thereof using dynamic multi-axis rotary motion under varying environmental conditions. Although various implementations of the apparatus have been described above with a certain degree of particularity, or with reference to one or more individual implementations, those skilled in the art could make numerous alterations to the disclosed implementations without departing from the spirit or scope of this invention. It is intended that all matter contained in the above description and shown in the accompanying drawings shall be interpreted as illustrative only of particular implementations and not limiting. Changes in detail or structure may be made without departing from the basic elements of the invention as defined in the following claims.

What is claimed is:

1. A testing apparatus for testing a device, the apparatus comprising: a test chamber adapted to hold the device; a first member affixed to and extending from the test chamber, the first member being adapted to rotate about a first axis; a second member adapted to rotate about a second axis, wherein the first axis and the second axis intersect; a joint structure coupling the first member and the second member to permit the first member to rotate the test chamber about the first axis while permitting the second member to rotate the first member about the second axis; and control circuitry adapted to operate the device while the first member rotates the test chamber about the first axis and the second member swings the test chamber about the second axis in a manner substantially simulating a user's swinging arm by rotating the first member about the second axis.

2. The testing apparatus of claim 1, wherein first member rotation is driven by a first motor.

3. The testing apparatus of claim 2, wherein second member rotation is driven by a second motor.

4. The testing apparatus of claim 2, wherein second member rotation is driven by a bevel gear or belt.

5. The testing apparatus of claim 1, wherein the test chamber comprises a structure for securing the device under test to the test chamber.

6. The testing apparatus of claim 5, wherein the test chamber further comprises a particulate counter device that counts particulate matter generated by the device during testing.

7. The testing apparatus of claim 5, wherein the test chamber further comprises one or more microphones.

8. The testing apparatus of claim 5, wherein the test chamber further comprises one or more sound wave generators.

9. The testing apparatus of claim 8, wherein the one or more sound wave generators is adapted to generate wave frequencies of about 10 Hz to about 20 KHz.

10. The testing apparatus of claim 5, wherein the test chamber further comprises one or more accelerometers.

11. The testing apparatus of claim 5, wherein the device has a rotating member when in an operational mode, and wherein the test chamber is oriented to the first axis of rotation such that the rotating member of the device is orthogonal to the first axis of rotation.

12. The testing apparatus of claim 5, wherein the device has a rotating member when in an operational mode, and wherein the test chamber is oriented to the first axis of rotation such that the rotating member of the device rotates in the same direction as the first axis of rotation.

13. The testing apparatus of claim 5, wherein the test chamber further comprises one or more vibrators.

14. The testing apparatus of claim 5, wherein the test chamber further comprises one or more temperature or humidity controls.

15. A multi-axis testing apparatus for testing a device comprising:
a test chamber adapted to hold the device, wherein the test chamber comprises a structure for securing the device to the test chamber and a microphone; a first member affixed to and extending from the test chamber, the first member being adapted to rotate about a first axis; a second member adapted to rotate about a second axis; and a joint structure coupling the first member and the second member to permit the first member to rotate the test chamber about the first axis while permitting the second member to rotationally oscillate the first member about the second axis in a manner substantially simulating a user's swinging arm.

16. The multi-axis testing apparatus of claim 15, wherein the test chamber further comprises one or more speakers.

17. The multi-axis testing apparatus of claim 15, wherein the test chamber further comprises one or more accelerometers.

18. The multi-axis testing apparatus of claim 15, wherein the test chamber further comprises one or more vibrators.

19. The multi-axis testing apparatus of claim 15, wherein the test chamber further comprises one or more temperature or humidity controls or vacuum control.

20. A method for testing a device, the method comprising: placing the device in a test chamber; rotating the test chamber about a first axis using a first rotating member; and simultaneously swinging the test chamber about a second axis by rotationally oscillating the first member about the second axis in a manner substantially simulating a user's swinging arm using a second rotating member, wherein the first axis and the second axis intersect.

21. The testing apparatus of claim 1, wherein the first member is further adapted to rotationally oscillate about the second axis.

22. The multi-axis testing apparatus of claim 15, wherein the first axis and the second axis intersect.

23. The multi-axis testing apparatus of claim 15, wherein first member rotation is driven by a first motor and second member rotation is driven by a second motor.

24. The method of claim 20, wherein first member rotation is driven by a first motor and second member rotation is driven by a second motor.

* * * * *